(12) United States Patent
Kleinert (10) Patent No.: US 9,354,204 B2
(45) Date of Patent: May 31, 2016

(54) ULTRASONIC TOMOGRAPHY SYSTEMS FOR NONDESTRUCTIVE TESTING

(75) Inventor: Wolf-Dietrich Kleinert, Bonn (DE)

(73) Assignee: General Electric Company, Schenectady, NY (US)

(*) Notice: Subject to any disclaimer, the term of this patent is extended or adjusted under 35 U.S.C. 154(b) by 597 days.

(21) Appl. No.: 13/274,152

(22) Filed: Oct. 14, 2011

(65) Prior Publication Data

US 2013/0096852 A1    Apr. 18, 2013

(51) Int. Cl.
*G01N 29/06*      (2006.01)
*G01N 29/265*     (2006.01)

(52) U.S. Cl.
CPC .......... *G01N 29/0672* (2013.01); *G01N 29/069* (2013.01); *G01N 29/0645* (2013.01); *G01N 29/265* (2013.01); *G01N 2291/0289* (2013.01); *G01N 2291/106* (2013.01)

(58) Field of Classification Search
CPC ...... A61B 8/00; A61B 8/4483; A61B 8/0825; A61B 8/13; A61B 8/14; A61B 8/15; A61B 8/463; A61B 29/262; A61B 29/069; A61B 29/2437; G01N 29/262; G01N 29/069; G01N 29/2437; B06B 1/0625; B06B 1/0633; B06B 1/0292; H04R 2201/401; G06T 11/003; G06T 11/006
USPC ............ 702/35–36, 39, 56, 124, 196; 73/571, 73/598–599, 603, 632–634; 600/437–447; 382/131
See application file for complete search history.

(56) References Cited

U.S. PATENT DOCUMENTS

| 4,279,157 A | | 7/1981 | Schomberg et al. |
| 4,581,581 A | * | 4/1986 | Pelc ............................... 324/309 |
| 4,706,499 A | | 11/1987 | Anderson |
| 4,843,884 A | * | 7/1989 | House et al. .................... 73/622 |
| 5,257,629 A | * | 11/1993 | Kitney et al. .................. 600/463 |
| 5,309,914 A | | 5/1994 | Iinuma |

(Continued)

FOREIGN PATENT DOCUMENTS

| CN | 1720007 A | | 1/2006 | |
| EP | 2211150 A1 | * | 7/2010 | ................ G01F 1/74 |

(Continued)

OTHER PUBLICATIONS

Tomikawa et al., Nondestructive Inspection of a Wooden Pole Using Ultrasonic Computed Tomography, Jul. 1986, IEEE Transactions on Ultrasonics, Ferroelectrics, and Frequency Control, vol. UFFC-33, No. 4.*

(Continued)

*Primary Examiner* — Mischita Henson
*Assistant Examiner* — Terence Stifter, Jr.
(74) *Attorney, Agent, or Firm* — Fletcher Yoder P.C.

(57) ABSTRACT

A system including a segmented transducer probe is provided. The segmented transducer probe includes a plurality of transducer segments adapted to transmit ultrasonic excitation signals into a test specimen and to receive echo signals resulting from the interaction of the ultrasonic excitation signals and the test specimen. The system also includes a processing system adapted to receive data from the segmented transducer probe that corresponds to the received echo signals and to utilize tomographic reconstruction methods to reconstruct an image corresponding to at least one volumetric slice of the test specimen.

20 Claims, 5 Drawing Sheets

(56) References Cited

U.S. PATENT DOCUMENTS

| | | | |
|---|---|---|---|
| 5,412,763 A * | 5/1995 | Knoplioch et al. | 345/424 |
| 5,544,655 A * | 8/1996 | Daigle | 600/447 |
| 5,718,228 A * | 2/1998 | Hiruta et al. | 600/437 |
| 5,899,861 A * | 5/1999 | Friemel | A61B 8/4254 128/916 |
| 5,991,239 A * | 11/1999 | Fatemi-Booshehri et al. | 367/164 |
| 6,171,247 B1 | 1/2001 | Seward et al. | |
| 6,347,551 B1 | 2/2002 | Turpening et al. | |
| 6,556,695 B1 * | 4/2003 | Packer et al. | 382/128 |
| 6,720,766 B2 | 4/2004 | Parker et al. | |
| 7,324,910 B2 | 1/2008 | Struempler et al. | |
| 7,542,544 B2 * | 6/2009 | Rubin et al. | 378/62 |
| 7,751,989 B2 | 7/2010 | Owens et al. | |
| 8,547,097 B2 * | 10/2013 | Gebhardt et al. | 324/307 |
| 2004/0087854 A1 * | 5/2004 | Ueda | 600/437 |
| 2005/0075565 A1 * | 4/2005 | Satoh | 600/437 |
| 2005/0119575 A1 * | 6/2005 | Ladabaum et al. | 600/459 |
| 2007/0239020 A1 * | 10/2007 | Iinuma et al. | 600/459 |
| 2008/0133200 A1 * | 6/2008 | Owens et al. | 703/13 |
| 2008/0154133 A1 * | 6/2008 | Shiki | G01S 7/52034 600/443 |
| 2008/0180580 A1 * | 7/2008 | Kadrmas | 348/744 |
| 2008/0276695 A1 | 11/2008 | Prater et al. | |
| 2009/0048789 A1 * | 2/2009 | Yu et al. | 702/39 |
| 2010/0199770 A1 | 8/2010 | Kleinert | |
| 2010/0215238 A1 * | 8/2010 | Lu et al. | 382/131 |
| 2010/0310145 A1 * | 12/2010 | Hashimoto et al. | 382/131 |
| 2010/0327868 A1 * | 12/2010 | Gebhardt et al. | 324/307 |
| 2011/0016977 A1 | 1/2011 | Guracar | |
| 2011/0016978 A1 | 1/2011 | Kleinert et al. | |
| 2011/0016979 A1 | 1/2011 | Oberdorfer et al. | |

FOREIGN PATENT DOCUMENTS

| | | |
|---|---|---|
| JP | S59202059 A | 11/1984 |
| JP | 2009281731 A | 12/2009 |
| WO | 2005009244 A1 | 2/2005 |

OTHER PUBLICATIONS

Tomography, Dec. 28, 2008, http://www.piletest.com/show.asp?page=tomography.*

Andrew Greensted, "Delay Sum Beamforming", Sep. 3, 2011, http://www.labbookpages.co.uk/audio/beamforming/delaySum.html.*

"Seeing With Sound—An introduction to Ultrasound", Oct. 1, 2010, Union College.*

Aaron Fenster, "3-Dimensional Ultrasound Imaging", Dec. 8, 2004, http://www.axisimagingnews.com/2004/12/3-dimensional-ultrasound-imaging/.*

Andrey Bulavinov, et al; "Industrial Application of Real-Time 3D Imaging by Sampling Phased Array"; 10th European Conference on Non-Destructive Testing (ECNDT); 2010; pp. 1-9.

Theobald Fuchs, et al.; "Multi-Modality Approaches for Complex Test Requirements"; International Symposium on NDT in Aerospace; Dec. 3-5, 2008, 7 pgs.; Furth, Germany; www.ndt.net/search/docs.php3?MainSource=81.

Hai-Dong Lang, et al.; "Continuous Wave Ultrasonic Tomography"; IEEE Transactions on Ultrasonics, Ferroelectrics, and Frequency Control, vol. 48, No. 1, Jan. 2001, pp. 285-292.

Liangzhong Xiang, et al.; "High Resolution Photoacoustic Standard CT for Quasi-3D Breast Cancer Imaging"; Symposium on Photonics and Optoelectronic (SOPO); IEEE 2010; 4 pgs.; MOE Key Laboratory of Laser Life Science & Institute of Laser Life Science, College of Biophotonics, South China Normal University, Guangzhou, China.

Kendall R. Waters; "Tomographic Imaging of an Ultrasonic Field in a Plane by Use of a Linear Array: Theory and Experiment"; IEEE Transactions on Ultrasonics, Ferroelectrics, and Frequency Control; vol. 52, No. 11, Nov. 2005, pp. 2065-2074.

EP Search Report and Written Opinion dated Mar. 18, 2014 issued in connection with corresponding EP Application No. 12187664.3.

CN Office Action; Application No. CN 201210385311.5; Dated Nov. 26, 2015; 8 pages.

* cited by examiner

ULTRASONIC TOMOGRAPHY SYSTEMS FOR NONDESTRUCTIVE TESTING

BACKGROUND OF THE INVENTION

The subject matter disclosed herein relates generally to nondestructive testing systems, and more particularly, to ultrasonic tomography systems for nondestructive testing.

Many industrial inspection applications rely on imaging techniques to determine the quality of industrial parts, such as pipes, pipe arrays, and so forth. For example, such inspection techniques may be utilized to determine the presence and/or location of one or more defects in an object, such as the presence of cracks, cavities, or other imperfections. One imaging modality that may be utilized to inspect objects for the presence of defects is ultrasonic tomography. Ultrasonic tomography is an imaging modality that employs ultrasound waves to probe the acoustic properties of the object of interest and to produce a corresponding image of the object, including any detectable defects. Generation of sound wave pulses and the detection of returning echoes is typically accomplished via transducers located in a transducer probe. Transducer probes typically include electromechanical elements that are capable of converting electrical energy into mechanical energy for transmission and that also are capable of converting mechanical energy back into electrical energy for receiving purposes.

Unfortunately, in some applications, the size of the defects relative to the size of the inspected object is relatively small, which makes it difficult to detect their presence in the reconstructed image of the inspected object. Furthermore, in many instances, multiple small defects may be spaced closely together, and while the combined area of the defects may be detectable via ultrasonic inspection, the size of each individual defect may be below the resolution of the system. Since the ability to identify defects present in the object is largely a function of the quality and resolution of the resulting image of the object, there exists a need for improved systems that overcome the aforementioned drawbacks.

BRIEF DESCRIPTION OF THE INVENTION

Certain embodiments commensurate in scope with the originally claimed invention are summarized below. These embodiments are not intended to limit the scope of the claimed invention, but rather these embodiments are intended only to provide a brief summary of possible forms of the invention. Indeed, the invention may encompass a variety of forms that may be similar to or different from the embodiments set forth below.

In a first embodiment, a system includes a segmented transducer probe having a plurality of transducer segments adapted to transmit ultrasonic excitation signals into a test specimen and to receive echo signals resulting from the interaction of the ultrasonic excitation signals and the test specimen. The system also includes a processing system adapted to receive data from the segmented transducer probe that corresponds to the received echo signals and to utilize tomographic reconstruction methods to reconstruct an image corresponding to at least one volumetric slice of the test specimen.

In a second embodiment, a method includes delivering a rotatable, non-axial-symmetric sound field to a test specimen and receiving echo signals resulting from an interaction of the rotatable, non-axial-symmetric sound field and the test specimen. The method also includes rotating the non-axial-symmetric sound field incrementally, delivering the rotated sound field to the test specimen and receiving further echo signals resulting from an interaction of the incrementally rotated, non-axial-symmetric sound field and the test specimen. The method further also includes utilizing the received echo signals and tomographic reconstruction methods to reconstruct an image corresponding to at least one volumetric slice of the test specimen.

In a third embodiment, a method includes delivering a rotatable, non-axial-symmetric sound field to a test specimen under an entrance angle of approximately zero degrees.

In a fourth embodiment, a method includes delivering a rotatable, non-axial-symmetric sound field to a test specimen under a variable entrance angle. The sound field may be delivered to the test specimen throughout multiple different entrance angles. In certain embodiments, the entrance angle is controlled by phased array techniques.

In a fifth embodiment, a method includes delivering a rotatable, non-axial-symmetric sound field exhibiting a two-fold, three fold, four fold, or n-fold rotational symmetry to a test specimen. In one embodiment, a highly unsymmetrical two-fold symmetry having an aspect ratio of approximately 1:2 or greater than approximately 1:2 may be delivered. For example, an aspect ratio of approximately 1:5 or higher may be utilized.

In a sixth embodiment, a device includes a segmented transducer probe. The transducer probe includes an array of transducer segments arranged such that the array exhibits a four-fold, five-fold, six-fold, or n-fold rotational symmetry, wherein an n-fold symmetry with n equal to or higher than 8 may be utilized. In some embodiments, n is equal to or greater than approximately 16, for example, equal to or greater than approximately 32. In certain embodiments, n may be a multiple of two or four. The transducer probe includes a plurality of opposite pairs of transducer segments. These pairs may include one, two, three, four or more adjacent transducer elements. In certain embodiments, the transducer segments may be substantially the same shape and size. The opposite pairs of transducer segments are adapted to be activated to generate a rotatable, non-axial-symmetric sound field.

In a seventh embodiment, a device includes a circular segmented transducer probe. The transducer probe includes an array of transducer segments circularly disposed about a rotation center point of the circular segmented transducer probe, the array having a plurality of opposite pairs of two, four, six, or any other suitable quantity of transducer segments. The opposite pairs of transducer segments are adapted to be activated to generate a rotatable, non-axial-symmetric sound field. In some embodiments, the transducer segments are circularly disposed about an inner diameter of the circular segmented transducer probe.

In an eighth embodiment, a segmented transducer probe may be utilized for generating a rotatable, non-axial-symmetric sound field. The transducer probe includes an array of transducer segments arranged such that the array exhibits a two-fold, three fold, four fold, or, n-fold rotational symmetry. For example, a two-fold symmetry may be exhibited in one embodiment. The transducer probe includes a plurality of opposite pairs of two, four, six, or any other suitable quantity of transducer segments. The opposite pairs of transducer segments are adapted to be activated to generate a rotatable, non-axial-symmetric sound field. In one embodiment, the transducer probe is circularly segmented, and the transducer segments are circularly disposed about an inner diameter of the circular segmented transducer probe.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF THE INVENTION

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements.

The disclosed embodiments are directed to ultrasonic tomography inspection systems capable of non-destructively probing a test specimen with ultrasonic energy to identify the presence and/or quantity of defects present inside the test specimen. To that end, disclosed embodiments include segmented transducer probes capable of generating a rotatable, non-axial-symmetric sound field that can be directed into the test specimen. For example, in one embodiment, a circular segmented transducer probe may include opposite pairs of transducer segments, and each transducer segment and the segment with which it is paired may transmit and receive signals concurrently. The resulting sound field may be substantially elliptical. By activating the adjacent opposite pairs, quadruples, or other suitable combination of transducers one after the other, the substantially elliptical sound field is rotated. The angle of rotation is dependent on the segmentation of the transducer. For each angle of rotation, the probe receives echo signals resulting from the interaction of the sound field with the test specimen and communicate data representing the echo signals to a processing system. The processing system is capable of employing a tomographic reconstruction method to the collected echo signals and to reconstruct a series of images corresponding to volumetric slices of the test specimen and is further capable of combining those images to reconstruct a volumetric representation of the test specimen. That is, the processing system may utilize any of a variety of known tomographic reconstruction methods to reconstruct the volumetric representations. For example, the processing system may utilize the echo signals to perform an algorithm that emulates the acquisition process of the echo signals in reverse along circular arcs. The reconstructed volumetric representation achieved through the disclosed embodiments may offer advantages over those obtained with existing ultrasonic tomography inspection systems since the rotatable, non-axial-symmetric sound field may increase the resolution of the reconstructed slices of the test specimen, thereby better enabling identification of defects.

Figure 1:
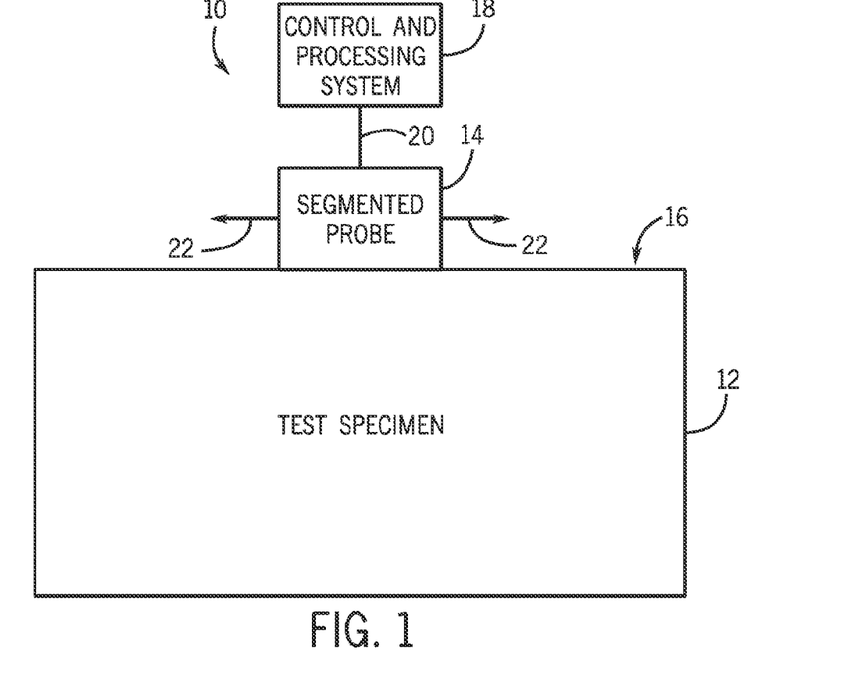
FIG. 1 is a schematic diagram of an embodiment of an ultrasonic testing system utilizing a segmented probe.

Turning now to the drawings, FIG. 1 is a schematic diagram depicting an embodiment of a testing system 10 that is capable of nondestructively probing a test specimen 12 to obtain structural information about the internal features of the test specimen 12. For example, the testing system 10 may be employed to identify the presence and/or location of one or more defects. The testing system 10 includes a segmented probe 14 positioned on a surface 16 of the test specimen 12 and a control and processing system 18 coupled to the segmented probe 14 via data connection 20. As discussed in more detail below, in certain embodiments, the control and processing system 18 may include a variety of components that enable the control and processing system 18 to both supply the segmented probe 14 with power and control signals and to receive echo signals from the segmented probe 14. To that end, the control and processing system may include various input and output devices, such as keyboards, data acquisition and processing controls, an image display panel, user interfaces, and so forth.

Further, it should be noted that the data connection 20 may transmit digital or analog data between the control and processing system 18 and the segmented probe 14. In this way, the data connection 20 may facilitate the bidirectional exchange of data between the segmented probe 14 and the control and processing system 18. For instance, in some embodiments, the control and processing system 18 may transmit control signals to the segmented probe 14 and receive matrices of digital data or analog signals that represent echo signals returned from the test specimen during an ultrasonic inspection method.

In certain embodiments, the segmented probe 14 includes arrays of transducer segments that produce ultrasonic excitation signals and receive echo signals resulting from an interaction of the ultrasonic excitation signals and the test specimen 12. Each individual transducer segment of the segmented probe 14 is generally capable of converting electrical energy into mechanical energy for transmission, and is further capable of converting mechanical energy into electrical energy for receiving purposes. As appreciated by one skilled in the art, in certain embodiments, the transducer segments may have one or more features that enable efficient transmission, detection, and processing of ultrasonic signals. Still further, each transducer segment may include traditional components, such as a piezoelectric ceramic, a matching layer, an acoustic absorber, and so forth. Additionally, the transducer segments may be of any type suitable for use with ultrasonic tomography, such as broad-bandwidth transducers, resonance transducers, and so forth. Indeed, a variety of transducer segments known to those skilled in the art may be employed in presently disclosed embodiments, and the features of the transducer segments of the segmented probe 14 for a given application may be implementation-specific.

During operation, the segmented probe 14 may be employed to probe the test specimen 12 to identify and/or quantify the presence of one or more defects in the structure of the test specimen 12. For example, the segmented probe 14 may be utilized to identify the presence of cracks, cavities, or other imperfections in the test specimen 12. To that end, the segmented probe 14 may be placed in a suitable location on the surface 16 of the test specimen 12, and the transducer segments of the segmented probe 14 may be fired in a desired pattern to produce a rotatable, non-axial-symmetric sound field that is transmitted into the test specimen 12. Once fired, pairs of transducer segments in the segmented probe 14 may receive echo signals that correspond to structural information of the test specimen 12. Subsequently, a neighboring pair of transducer elements is activated. Firing these adjacent transducer elements leads to a rotation of the sound field delivered to the test specimen. By continuously moving from one pair of transducer elements to the other, the sound field can be rotated by approximately 180° leading to the starting configuration of the sound field. Once the desired transmitting and receiving cycles are complete, which can be accomplished by a 180° rotation of the sound field showing a two-fold rotational symmetry, the segmented probe 14 may be moved about the surface 16 of the test specimen 12 to a variety of positions to obtain data corresponding to the volume of the test specimen 12. For example, the segmented probe 14 may be translated along the width of the test specimen 12, as indicated by arrows 22, or along the length of the test specimen 12 to obtain similar data from a variety of positions on the surface 16 of the test specimen 12.

Figure 2:
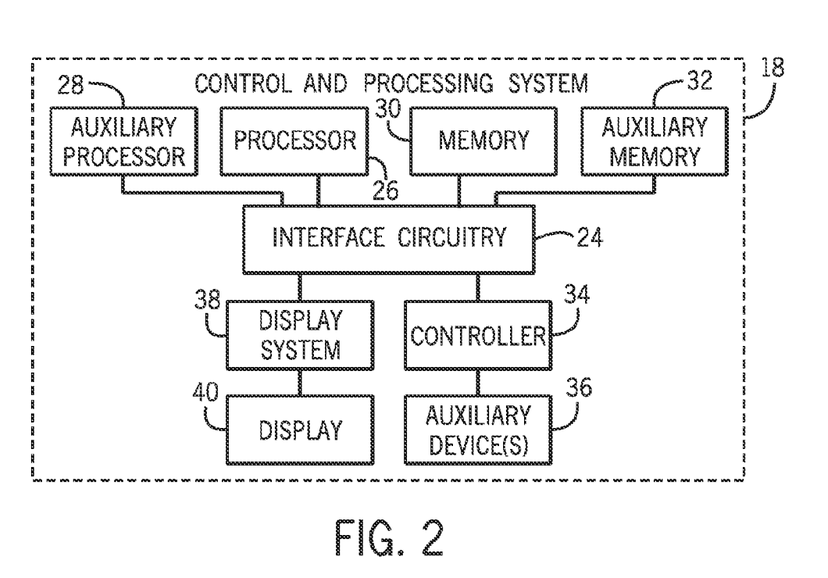
FIG. 2 is a block diagram depicting an embodiment of a control and processing system that can be used with the segmented probe of FIG. 1.

FIG. 2 is a block diagram depicting an embodiment of the control and processing system 18 of FIG. 1 that may be employed to control and/or power the segmented probe 14. In the depicted embodiment, the control and processing system 18 includes interface circuitry 24 that enables communication of data between components of the control and processing system 18. The components in the depicted system 18 include a processor 26, an auxiliary processor 28, a memory 30, an auxiliary memory 32, a controller 34, auxiliary devices 36, a display system 38, and a display 40, although the components in any embodiment are implementation-specific and may depend on factors such as the type of segmented probe 14 being utilized.

During operation, when the control and processing circuitry 18 is receiving information, the interface circuitry 24 receives data from the segmented probe 14 via the data connection 20. The interface circuitry 24 may receive data that corresponds to the echo signals received by the segmented probe 14 after the excitation signals have interacted with the test specimen 12. This data is then transmitted to the processor 26 and/or the auxiliary processor 28, where a tomographic reconstruction method may be utilized to reconstruct images corresponding to volumetric slices of the test specimen 12. These volumetric slices may then be combined to reconstruct a volumetric representation of the test specimen 12. In certain embodiments, the processor 26 may include signal processing circuitry adapted to perform the foregoing functions, and the auxiliary processor 28 may include circuitry programmed to further process the data, for example, to filter the reconstructed slices or the reconstructed volumetric representation. To that end, the processor 26 and/or the auxiliary processor 28 may include various suitable microcontrollers, microprocessors, or other desired circuitry. Further, in certain embodiments, the auxiliary processor 28 may be integrated with the circuitry of the processor 26. Still further, the processor 26 may also execute algorithms that control the operating functions of the test system.

The generated volumetric slices and/or complete volumetric representations of the test specimen 12 may then be transmitted to the display system 38 via the interface circuitry 24. The display system 38 generally includes circuitry adapted to display volumetric representations of the test specimen 12 on the display 40. For example, the display system 38 may include memory for storing the received data, a graphics card, a user interface for communicating with an operator, and so forth.

Additionally, the interface circuitry 24 may store the data received from the segmented probe 14, the processor 26, and/or the display system 38 to memory 30 and/or to auxiliary memory 32. In certain embodiments, the memory 30 may be utilized to store data relating to programs executed by the processor 26 and/or the auxiliary processor 28, and the auxiliary memory 32 may be utilized to store received image data and/or data that may be loaded into the memory 30 prior to execution by the processor 26. The memory 30 and/or the auxiliary memory 32 may include volatile or non-volatile memory, such as a computer readable media, read only memory (ROM), random access memory (RAM), magnetic storage memory, optical storage memory, or a combination thereof.

Furthermore, a variety of control parameters may be stored in the memory 30 along with code designed to provide a specific output during operation of the testing system 10. For example, the memory 30 may store executable algorithms that the controller 34 may selectively access depending on the auxiliary devices 36 that are connected to the given system. The auxiliary devices 36 may include a keyboard, a printer, a recording device, a network interfacing device, a combination thereof, or any other external device that may be desired in the testing system 10. Further, the controller 34 may access the memory 30 to access the algorithms corresponding to the particular auxiliary devices 36 included in the system.

Figure 3:
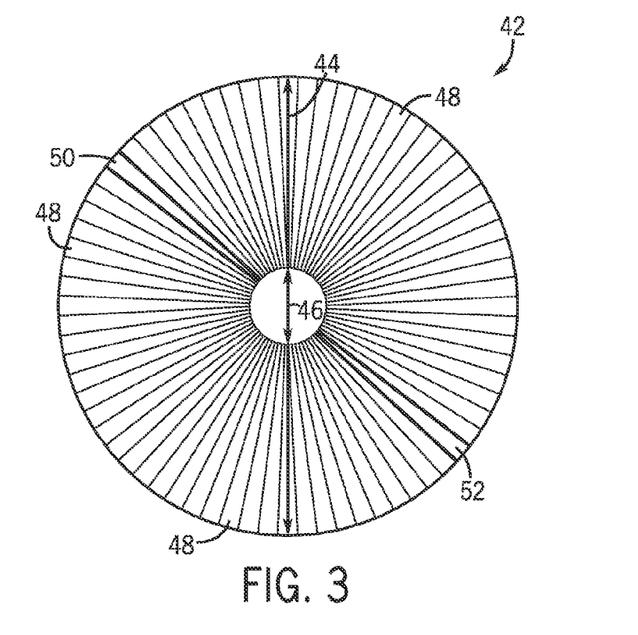
FIG. 3 depicts an embodiment of a segmented transducer probe that can be employed in the ultrasonic testing system of FIG. 1.

FIG. 3 depicts an embodiment of a circular segmented transducer probe 42 that may be employed in the testing system 10 of FIG. 1 to generate a rotatable, non-axial-symmetric sound field. The circular segmented transducer probe 42 has an outer diameter 44 and an inner diameter 46 and includes a plurality of transducer segments 48 arranged in a circular array. In certain embodiments, the inner diameter 46 of the circular probe 42 may be approximately zero, depending on one or more manufacturing parameters. The circular array of transducer segments 48 includes a plurality of pairs of opposite transducer segments, and the transducer segments within each pair may be adapted to receive and transmit signals concurrently with one another, as described in more detail below. In the depicted embodiment, a first transducer segment 50 and a second transducer segment 52 form a pair of opposite transducer segments. That is, the first transducer segment 50 and the second transducer segment 52 are disposed on opposite sides of the segmented transducer probe 42 about the inner diameter 46. Although only the pair of transducer segments 50 and 52 is highlighted in the depicted embodiment, each set of oppositely disposed transducer segments 48 in the circular array forms a pair of opposite transducer segments. It should be noted that although in the illustrated embodiment, each pair includes two segments, in some embodiments each pair may include multiple segments (e.g., a pair includes two segments opposite another two segments).

It should be noted that although the segmented transducer probe 42 of FIG. 3 is circular in shape, the segmented transducer probe may be any of a variety of suitable shapes and sizes. Additionally, the transducer segments may be dimensioned to accommodate the overall shape of the segmented transducer probe. For example, in one embodiment, the segmented probe may be rectangular, and, accordingly, the transducer segments may be rectangular in shape as well. Indeed, the configuration of the segmented transducer probe may be implementation-specific, and the chosen configuration may be partially or wholly determined by the size and shape of the test specimen.

Figure 4:
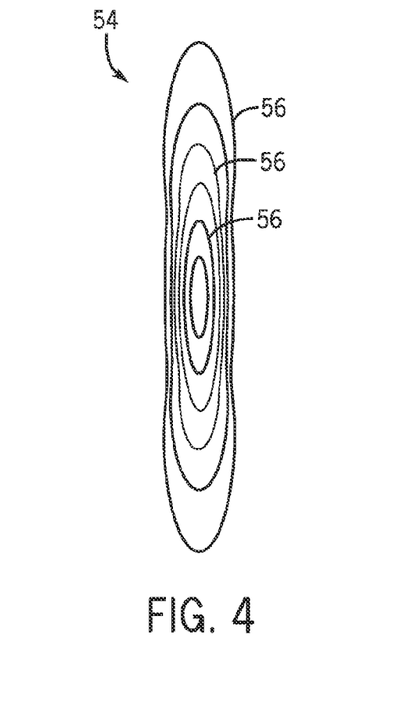
FIG. 4 depicts an embodiment of a rotatable non-axial-symmetric sound field that can be generated with the segmented transducer probe of FIG. 3.

During operation, the segmented transducer probe 42 of FIG. 3 may be employed to produce a rotatable, non-axial-symmetric sound field 54, as depicted in FIG. 4. The rotatable, non-axial-symmetric sound field 54 includes non-axial-symmetric isobars 56 that can be transmitted into a test specimen to nondestructively test the specimen for the presence, absence, location, and/or quantity of one or more defects. That is, the non-axial-symmetric sound field is substantially elliptically. In one embodiment, to generate the non-axial-symmetric sound field 54, the segmented transducer probe 42 is placed in a desired location on the test specimen, and the desired transducer segments are activated to produce ultrasonic excitation signals that are transmitted into the test specimen. In an embodiment, the pair of opposite transducer segments 50 and 52 is fired, and the returning echo signal is received by the desired two of the transducer segments 48. This process may be sequentially repeated until all of the pairs of opposite transducer segments receive the returning echo signals. In another embodiment, however, all the transducer segments 48 in the circular array may be fired concurrently with one another, and each pair of opposite transducer segments independently receives the returning echo signals. Regardless of the manner in which the data is acquired at the location of the segmented probe 42, data is received for a multiplicity of rotation angles of the non-axial-symmetric sound field. Once the data is received, the segmented probe 42 is moved to the next location on the test specimen surface, and the process is repeated. In this manner, data regarding the entire internal structural volume of the test specimen may be obtained and processed by the processing and control system 18 to identify the presence and quantity of defects.

Figure 5:
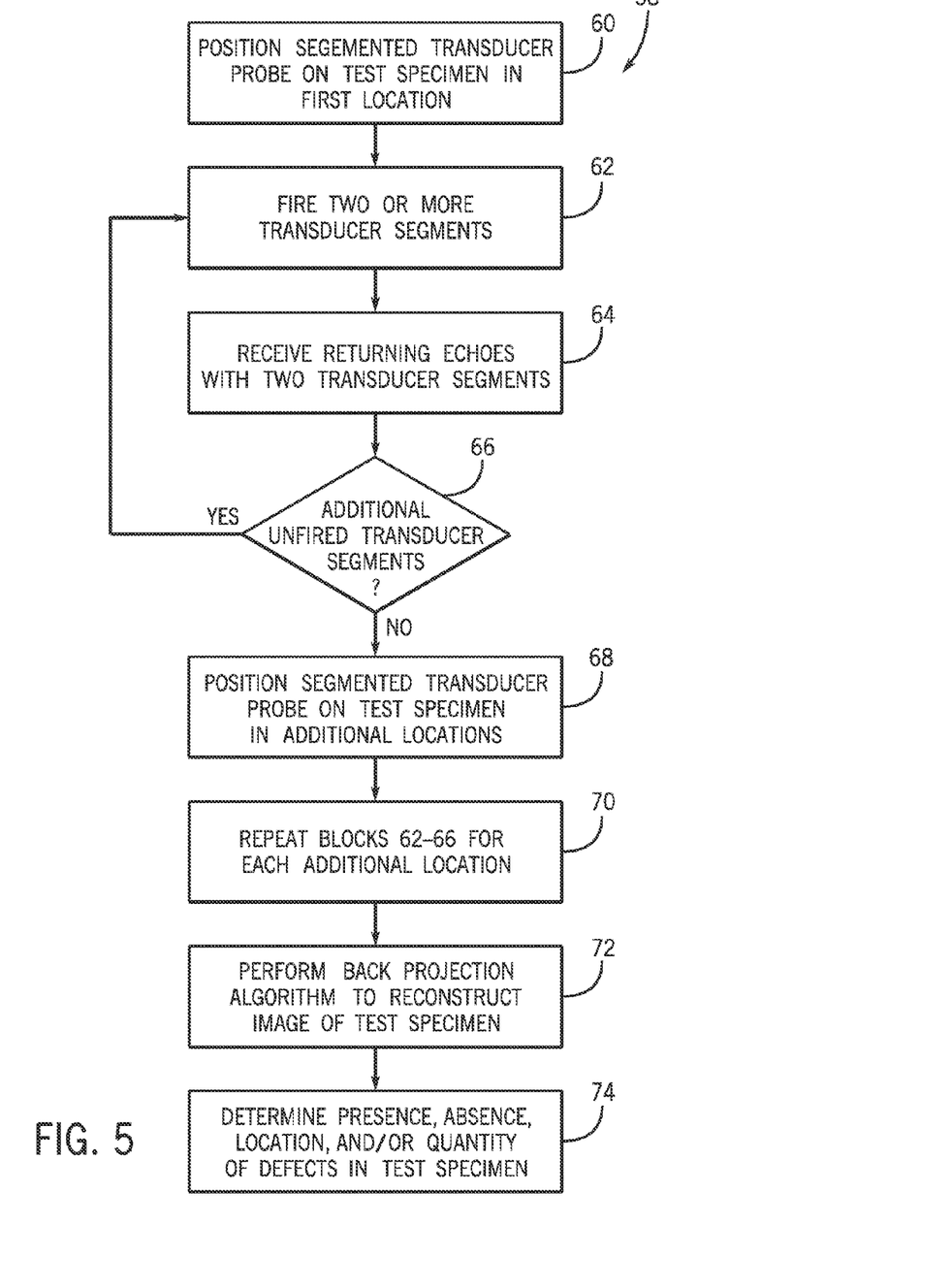
FIG. 5 is a flow chart of an embodiment of a method that can be employed to generate a reconstructed image of a test specimen by using the segmented transducer probe of FIG. 3.

FIG. 5 is a flow chart depicting a method 58 that may be utilized to probe a test specimen with a segmented probe to obtain defect information about the structure of the test specimen. The method 58 may begin by positioning (block 60) the segmented probe on the test specimen in the first location on the surface of the test specimen. Two or more transducer segments may then be fired (block 62), thus transmitting the rotatable, non-axial-symmetric sound field into the test specimen. As noted above, the transducer segments may be fired sequentially in pairs or all the transducer segments in the array may be concurrently fired. The echo signals resulting from an interaction of the non-axial-symmetric sound field with the test specimen are then received (block 64) by a pair of transducer segments. The method 58 may then continue by determining (block 66) whether additional unfired transducer segments are present. If unfired transducer segments are present, an additional pair of opposite transducer segments may be fired (block 62), and the process may be repeated.

However, if all transducer segments have been fired, the segmented transducer may be translated (block 68) along the surface of the test specimen to the desired additional locations. The acquisition process may then be repeated (block 70) at each additional location, as described above with respect to blocks 62-66. After a set of data corresponding to the volume of the test specimen is acquired, the data may be transmitted to the control and processing circuitry, and a back projection algorithm may be utilized (block 72) to reconstruct an image of the test specimen. The reconstructed image may be a volumetric slice of the test specimen or an entire volumetric representation of the test specimen.

The depicted method 58 also includes determining (block 74) the presence, absence, location, and/or quantity of defects in the test specimen. However, it should be noted that while in some embodiments, the test system may determine the presence, absence, location and/or quantity of defects through the control and processing circuitry, in other embodiments, this step may be performed by an operator. That is, in certain embodiments, the testing system may be adapted to acquire and process the data corresponding to structural information about the test specimen, and an operator may analyze the data to obtain defect information about the structure.

Figure 6:
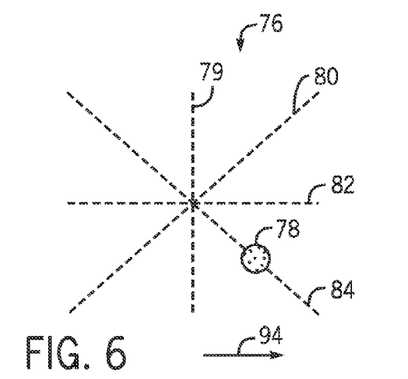
FIG. 6 is a schematic diagram depicting an embodiment of a sound field rotation about a defect in a test specimen at a first probe location.
Figure 7:
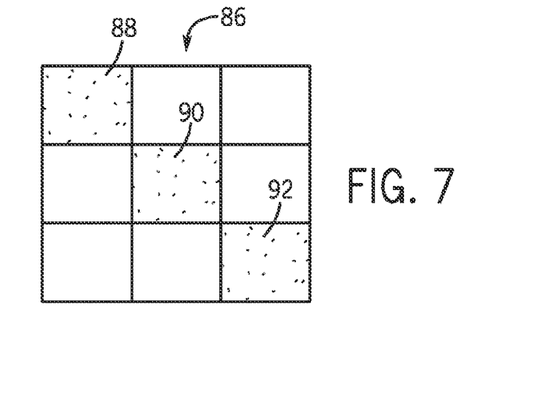
FIG. 7 depicts an embodiment of a matrix that can be generated with the sound field of FIG. 6.

FIGS. 6-11 schematically depict an embodiment of a tomographic reconstruction method that can be employed to reconstruct a representation of the test specimen. Specifically, FIG. 6 depicts a rotated sound field 76 being employed to probe a defect 78 that may be present in a test specimen. The rotated sound field 76 is generated while the segmented probe is positioned in a first location on the surface of the test specimen. As shown, the rotated sound field 76 includes a first sound field rotation 79, a second sound field rotation 80, a third sound field rotation 82, and a fourth sound field rotation 84. At each sound field rotation, echo signals resulting from interaction of the sound field with the test specimen are obtained. A matrix 86, as shown in FIG. 7, is generated that captures the received information from the first scan position. The matrix 86 may be stored to memory 30 or auxiliary memory 32 in some embodiments. For example, since sound field rotations 79, 80, and 82 do not interact with the defect 78, these sound field rotations do not contribute positive values to the matrix 86. However, because sound field rotation 84 does interact with defect 78, this interaction is recorded, and the amplitude of the received signal is stored in blocks 88, 90, and 92 of the matrix 86.

Figure 8:
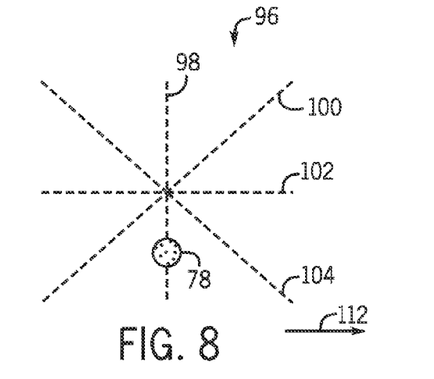
FIG. 8 is a schematic diagram depicting an embodiment of a sound field rotation about a defect in a test specimen at a second probe location.
Figure 9:
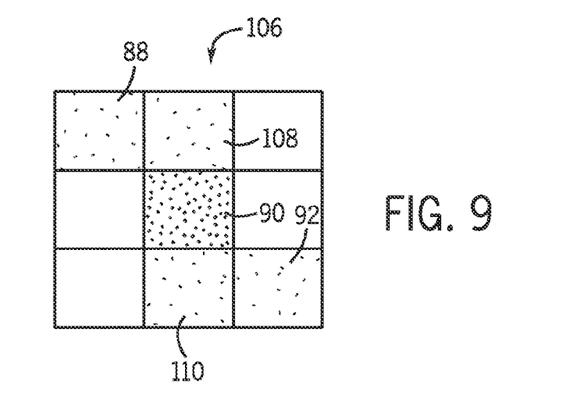
FIG. 9 depicts an embodiment of a matrix that can be generated with the sound field of FIG. 8.

The segmented probe is then translated to a second position along the part, as illustrated by arrow 94. That is, the segmented probe is moved along the test specimen, as shown by arrows 22 in FIG. 1. Subsequently, another rotated sound field 96 is generated, as shown in FIG. 8. As before, the rotated sound field 96 includes a first sound field rotation 98, a second sound field rotation 100, a third sound field rotation 102, and a fourth sound field rotation 104. Here again, at each sound field rotation, echo signals resulting from interaction of the sound field with the test specimen are obtained. Another matrix 106, as shown in FIG. 9, is generated. The matrix 106 represents a sum of a probe matrix obtained from probing with the sound field 76 and a shifted probe matrix obtained from probing with the sound field 96. For example, sound field rotations 100, 102, and 104 do not interact with the defect 78 when the segmented probe is positioned in the second location, and, accordingly, these sound field rotations do not contribute positive values to the matrix 106. However, sound field rotation 98 does interact with defect 78, and this interaction is recorded in a second probe matrix corresponding to the second probe location. This second probe matrix is shifted and added to the first probe matrix to generate matrix 106. The blocks 108, 90, and 110 of the matrix 106 reflect the amplitude of the signal recorded after probing with sound field 96.

Figure 10:
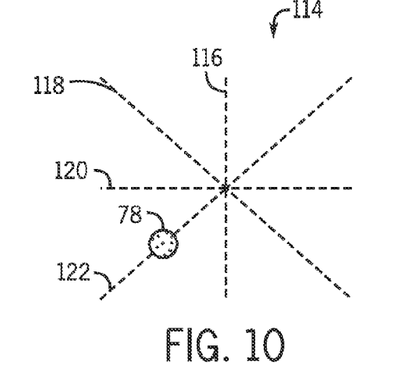
FIG. 10 is a schematic diagram depicting an embodiment of a sound field rotation about a defect in a test specimen at a third probe location.
Figure 11:
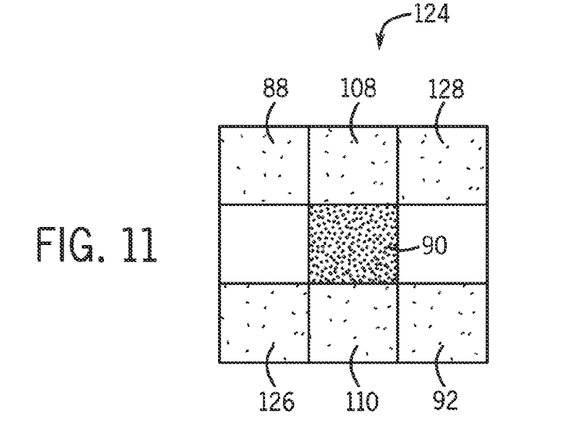
FIG. 11 depicts an embodiment of a matrix that can be generated with the sound field of FIG. 10.

The segmented probe is again translated to another position along the part, as illustrated by arrow 112. That is, the segmented probe is moved further along the width of the test specimen, as shown by arrows 22 in FIG. 1. An additional rotated sound field 114 is then generated, as shown in FIG. 10. The rotated sound field 114 includes sound field rotations 116, 118, and 120 that do not interact with the defect 78 when the segmented probe is positioned in the third location. Additionally, the sound field 114 includes a sound field rotation 122 that does interact with the defect 78, and this interaction is recorded in a third probe matrix corresponding to the third probe location. This third probe matrix is shifted and added to the matrix 106 to generate matrix 124, as shown in FIG. 11. The blocks 126, 90, and 128 of the matrix 124 reflect the amplitude of the signal recorded after probing with sound field 114. In this way, the matrix 124 includes the information from the first probe matrix, a shifted second probe matrix, and a shifted third probe matrix. This process is repeated for all the desired scan positions, thus resulting in a reconstructed slice of the test specimen. It should be noted that after generating the image matrix, which reflects the information stored in the plurality of probe matrices, one or more filters may be used to further improve the image quality. For example, in one embodiment, an edge-sharpening filter, such as a Shepp-Logan-Filter, may be utilized.

It should be noted that the control and processing circuitry may utilize the matrix 124 to generate one or more volumetric slices of the test specimen. In this way, the segmented probes disclosed herein may be utilized in combination with a tomographic reconstruction method to nondestructively obtain volumetric information about the test specimen. Again, by utilizing a rotatable, non-axial-symmetric sound field to probe the test specimen, the resolution of the testing system may be increased as compared to traditional systems, thus potentially enabling better resolution of defects present in the test specimen.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A system, comprising:
a segmented transducer probe comprising a plurality of transducer segments arranged in a plurality of opposite pairs of transducer segments, wherein each opposite pair of transducer segments of the plurality of opposite pairs of transducer segments comprises a first transducer segment and a second transducer segment, the first transducer segment of each opposite pair is disposed on an opposite side of the segmented transducer probe than the second transducer segment of the respective opposite pair, each transducer segment of the plurality of transducer segments is configured to transmit ultrasonic excitation signals into a surface of a test specimen and to receive echo signals resulting from an interaction of the ultrasonic excitation signals and the test specimen, and the plurality of transducer segments is disposed in a plane; and
a processing system configured to control the segmented transducer probe to sequentially activate the plurality of opposite pairs of transducer segments, to receive data from the segmented transducer probe that corresponds to the received echo signals from the plurality of opposite pairs of transducer segments, and to utilize a tomographic reconstruction method to reconstruct an image corresponding to at least one volumetric slice of the test specimen;
wherein sequential activation of the plurality of opposite pairs of transducer segments comprises:
activating a first opposite pair of the plurality of opposite pairs of transducer segments to transmit the ultrasonic excitation signals into the test specimen and to receive the echo signals from the test specimen via the first transducer segment and the second transducer segment of the first opposite pair;
deactivating the first opposite pair of the plurality of opposite pairs of transducer segments to stop transmission of the ultrasonic excitation signals and to stop reception of the echo signals via the first transducer segment and the second transducer segment of the first opposite pair; and
activating a second opposite pair of the plurality of opposite pairs of transducer segments to transmit the ultrasonic excitation signals into the test specimen and to receive the echo signals from the test specimen via the first transducer segment and the second transducer segment of the second opposite pair.

2. The system of claim 1, wherein the processing system is configured to utilize the tomographic reconstruction method to reconstruct a plurality of volumetric slices of the test specimen and to combine the plurality of volumetric slices to reconstruct a volumetric representation of the test specimen.

3. The system of claim 1, wherein the plurality of opposite pairs of transducer segments is spatially arranged in a circular arrangement in the plane about an axis, the axis is disposed between the first transducer segment and the second transducer segment of each opposite pair of transducer segments, and the processing system is configured to sequentially activate adjacent opposite pairs of transducer segments about the circular arrangement.

4. The system of claim 1, wherein the transducer segments of an opposite pair of transducer segments are configured to transmit the ultrasonic excitation signals and to receive the echo signals concurrently when the opposite pair of transducer segments of the plurality of transducer segments is sequentially activated.

5. The system of claim 1, wherein the segmented transducer probe comprises a rotation center point within the plane and an array of opposite pairs of transducer segments spatially disposed within the plane about the rotation center point, wherein each opposite pair of transducer segments in the array of opposite pairs is configured to transmit the ultrasonic excitation signals as a rotatable, non-axial-symmetric sound field relative to the rotation center point.

6. The system of claim 1, wherein the processing system comprises a display system configured to display a visual representation of the reconstructed image of the test specimen.

7. The system of claim 1, wherein the processing system is configured to evaluate the reconstructed image to determine at least one of a presence of defects present in the test specimen, an absence of defects present in the test specimen, a location of defects present in the test specimen, or a quantity of defects present in the test specimen.

8. A system, comprising:
a circular segmented transducer probe, comprising:
an array of transducer segments circularly disposed in a plane about an inner diameter of the circular segmented transducer probe and comprising a plurality of opposite pairs of transducer segments, wherein each opposite pair of transducer segments comprises a first transducer segment disposed on an opposite side of the inner diameter than a second transducer segment of the respective opposite pair;
wherein each opposite pair of transducer segments of the plurality of opposite pairs of transducer segments is configured to generate a rotatable, non-axial-symmetric sound field into a surface of a test specimen when the respective opposite pair of transducer segments is activated, the opposite pairs of the plurality of opposite pairs of transducer segments are to be sequentially activated in a desired pattern in operation of the circular segmented transducer probe to rotate the generated non-axial-symmetric sound field.

9. The system of claim 8, wherein each of the opposite pairs of transducer segments comprises a first transducer segment and a second transducer segment that are configured to concurrently receive echo signals resulting from an interaction of the rotatable, non-axial-symmetric sound field and the test specimen when the respective opposite pair is activated, wherein the first and second transducer segment of the respective opposite pairs are configured to concurrently generate the rotatable, non-axial-symmetric sound field and receive the echo signals when the respective opposite pair is activated.

10. The system of claim 9, comprising a processor configured to receive data from the circular segmented transducer probe that corresponds to the received echo signals and to utilize a tomographic reconstruction method to reconstruct an image corresponding to at least one volumetric slice of the test specimen.

11. The system of claim 10, wherein the processor is configured to utilize a tomographic reconstruction method to reconstruct a plurality of volumetric slices of the test specimen and to combine the plurality of volumetric slices to reconstruct a volumetric representation of the test specimen.

12. The system of claim 9, wherein the processor is configured to evaluate the reconstructed image to determine at least one of a presence of defects present in the test specimen, an absence of defects present in the test specimen, a location of defects present in the test specimen, or a quantity of defects present in the test specimen.

13. The system of claim 8, wherein the desired pattern comprises sequential activation of adjacent opposite pairs of the plurality of opposite pairs of transducer segments in a circumferential direction about the inner diameter of circular segmented transducer probe.

14. A method, comprising:
positioning a segmented transducer probe at a first location on a surface of a test specimen, wherein the segmented transducer probe comprises a plurality of opposite pairs of transducer segments, wherein each opposite pair of transducer segments comprises a first transducer segment disposed on an opposite side of the segmented transducer probe than a second transducer segment;
rotating a first rotatable, non-axial-symmetric sound field at the first location, comprising:
sequentially activating a first opposite pair of transducer segments and a second opposite pair of transducer segments of the plurality of opposite pairs of transducer segments, wherein activating each respective opposite pair comprises:
transmitting, from the respective opposite pair of transducer segments of the transducer probe, the first rotatable, non-axial-symmetric sound field to the test specimen at the first location; and
concurrently receiving, at the respective opposite pair of transducer segments of the transducer probe, first echo signals resulting from a first interaction between the first rotatable, non-axial-symmetric sound field and the test specimen at the first location;
translating the segmented transducer probe to a second location along the surface of the test specimen, wherein translating the segmented transducer probe comprises moving the segmented transducer probe in a plane parallel to the surface of the test specimen;
rotating a second rotatable, non-axial-symmetric sound field at the second location, comprising:
sequentially activating the first opposite pair of transducer segments and the second opposite pair of transducer segments of the plurality of opposite pairs of transducer segments, wherein activating each opposite pair comprises:
transmitting, from the respective opposite pair of transducer segments of the transducer probe, the second rotatable, non-axial-symmetric sound field to the test specimen at the second location; and
concurrently receiving, at the respective opposite pair of transducer segments of the transducer probe, second echo signals resulting from a second interaction between the second rotatable, non-axial-symmetric sound field and the test specimen at the second location; and
utilizing the received first echo signals, the second echo signals, and a tomographic reconstruction method disposed in a processing system to reconstruct an image corresponding to at least one volumetric slice of the test specimen at the first location.

15. The method of claim 14, wherein rotating the first rotatable, non-axial-symmetric sound field comprises sequentially activating opposite pairs of transducer segments of the segmented transducer probe in a desired pattern.

16. The method of claim 14, wherein utilizing the received first echo signals, the second echo signals, and the tomographic reconstruction method to reconstruct the image comprises generating matrices of a numerical representation of the received first echo signals and second echo signals corresponding to the respective first location and the second location, and summing the generated matrices.

17. The method of claim 14, comprising reconstructing a volumetric representation of the test specimen from the at least one volumetric slice and displaying the volumetric representation on a display.

18. The method of claim 14, wherein rotating the first rotatable, non-axial-symmetric sound field comprises sequentially activating adjacent opposite pairs of transducer segments of the segmented transducer probe.

19. The method of claim 14, wherein the plurality of opposite pairs of transducer segments are disposed about an inner diameter of the segmented transducer probe.

20. The method of claim 14, comprising evaluating the reconstructed image to determine at least one of a presence of defects present in the test specimen, an absence of defects present in the test specimen, a location of defects present in the test specimen, or a quantity of defects present in the test specimen.

* * * * *